(12) United States Patent
Wittland et al.

(10) Patent No.: US 10,537,688 B2
(45) Date of Patent: Jan. 21, 2020

(54) SAFETY DEVICE FOR PREFILLED SYRINGES

(71) Applicants: Gerresheimer Regensburg GmbH, Regensburg (DE); Gerresheimer Buende GmbH, Buende (DE)

(72) Inventors: Frank Wittland, Buende (DE); Maximilian Vogl, Mantel (DE)

(73) Assignees: Gerresheimer Regensburg GmbH, Regensburg (DE); Gerresheimer Buende GmbH, Buende (DE)

( * ) Notice: Subject to any disclaimer, the term of this patent is extended or adjusted under 35 U.S.C. 154(b) by 33 days.

(21) Appl. No.: 15/573,032

(22) PCT Filed: Jun. 3, 2016

(86) PCT No.: PCT/EP2016/062713
§ 371 (c)(1),
(2) Date: Nov. 9, 2017

(87) PCT Pub. No.: WO2016/202614
PCT Pub. Date: Dec. 22, 2016

(65) Prior Publication Data
US 2018/0161516 A1 Jun. 14, 2018

(30) Foreign Application Priority Data
Jun. 15, 2015 (EP) ..................................... 15172153

(51) Int. Cl.
*A61M 5/32* (2006.01)
(52) U.S. Cl.
CPC .......... *A61M 5/3272* (2013.01); *A61M 5/326* (2013.01); *A61M 2005/3267* (2013.01)
(58) Field of Classification Search
CPC ................. A61M 5/3272; A61M 5/326; A61M 2005/3267
See application file for complete search history.

(56) References Cited

U.S. PATENT DOCUMENTS 2,834,346 A 5/1958 Adams
4,932,940 A 6/1990 Walker et al.
(Continued)

FOREIGN PATENT DOCUMENTS

FR 2884723 A1 10/2006

OTHER PUBLICATIONS

Canadian First Office Action, dated Sep. 5, 2018 in Canadian Patent Application No. 2,984,508, a related application, 3 pp.
(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

A syringe member comprising a safety device to prevent pricking injuries; the syringe member comprises a pricking element, and the safety device includes at least one guided pin and a recess which forms a guide slot for guiding the guided pin in a longitudinal direction of the syringe member during movement of the syringe member relative to the safety device; said guide slot includes a first slot region and a second slot region which are separated by a notional separation line extending in a longitudinal direction of the syringe member; the guided pin can be placed in the first slot region in a starting position and can be moved from the first slot region into the second slot region into a final position by having the guided pin cross the separation line when a distal end of the pricking element is located at the level of an exit opening of the safety device.

14 Claims, 7 Drawing Sheets

(56) References Cited

U.S. PATENT DOCUMENTS

| | | |
|---|---|---|
| 9,962,497 B2 * | 5/2018 | Takemoto ........... A61M 5/3213 |
| 2009/0024093 A1 | 1/2009 | Carrel et al. |
| 2011/0319833 A1 | 12/2011 | Chun |
| 2018/0104421 A1 | 4/2018 | Wittland et al. |
| 2018/0110934 A1 | 4/2018 | Wittland et al. |
| 2018/0133409 A1 | 5/2018 | Fraas et al. |
| 2018/0161511 A1 | 6/2018 | Fraas et al. |
| 2018/0161512 A1 | 6/2018 | Wittland et al. |

OTHER PUBLICATIONS

International Search Report with Written Opinion corresponding to International Patent Application No. PCT/EP2016/062713, dated Sep. 1, 2016.

* cited by examiner

SAFETY DEVICE FOR PREFILLED SYRINGES

CROSS-REFERENCE TO RELATED APPLICATIONS

This application is a U.S. National Stage Application filed under 35 U.S.C. § 371 of International Application No. PCT/EP2016/062713, filed Jun. 3, 2016, which claims the benefit of European Application No. EP 15172153.7, filed Jun. 15, 2015. Both of these applications are hereby incorporated by reference in their entireties.

The invention relates to a syringe member comprising a safety device at the end thereof to prevent pricking injuries; the syringe member comprises a pricking element at the end thereof, and the safety device includes at least one guided pin and a recess which forms a guide slot for guiding the guided pin in a longitudinal direction of the syringe member during a movement of the syringe member relative to the safety device.

Safety devices for preventing pricking injuries are known in the art, which are mounted so as to surround the entire syringe once the syringes have been filled.

However, these safety apparatuses increase the dimensions, in terms of both the sheer size and the weight of the syringe to be used, so that syringes having safety apparatuses of this type are considerably more difficult to handle.

Furthermore, safety devices are designed such that a syringe can already be rendered unusable, for example if the injection procedure is discontinued, without the needle tip having even left the safety device. The syringe is therefore already unusable before actually making contact with the patient and even if it has not been contaminated.

This is the complete opposite for other known safety devices. The needle tip is moved into a safe position only after it has already left the safety device. This has the serious disadvantage that an injection could be repeated even though the needle has already been in contact with the patient. It is therefore possible for a person to come into contact with a contaminated needle and to be injured or even infected thereby.

The object of the present application is therefore to provide a syringe member having a safety apparatus, which no longer has the disadvantages of the prior art.

This problem addressed is solved by a syringe member comprising a safety device arranged at one end of said member for preventing pricking injuries, the syringe member comprising a pricking element that is arranged at one end thereof and the safety device comprising at least one recess and at least one guided pin, the recess forming a guide slot for guiding the guided pin in a longitudinal direction of the syringe member when the syringe member moves relative to the safety device, the guide slot comprising a first and a second slot region, which are separated by a notional separation line extending in a longitudinal direction of the syringe member, and it being possible for the guided pin to be placed in a starting position in the first slot region and to be moved from the first slot region into a final position in the second slot region by having the guided pin cross the separation line when a distal end of the pricking element is located at the level of an exit opening of the safety device during the movement of the syringe member relative to the safety device.

In this context, the expression "arranged at one end" should be understood to mean that the particular structural element is arranged at a distal end. The safety device and the pricking element are therefore arranged at the distal end of the syringe member.

The term "pricking element" should be understood to mean a needle, a cannula, a lancet or the like.

A "starting position" describes a position, preferably of the guided pin, which corresponds to an unused syringe, i.e. before a syringe is used.

A "final position" describes a position in which the syringe in the present case has already been used. If the guided pin has reached the final position, it is no longer possible to use the syringe again.

According to the invention, the guided pin can be moved from the first slot region to the second slot region. Said guided pin is moved when it passes a notional separation line that separates the first and the second slot regions from one another. If the guided pin is in the first slot region, i.e. in a starting position, the syringe has not yet been actuated, i.e. the needle has not yet left the safety device. If the guided pin is in the second slot region, the needle has already left the safety device, making injection possible. When transitioning from the first slot region to the second slot region, i.e. at the exact point when the guided pin passes the dividing line, the distal end of the pricking element, for example the needle, is at the level of the exit opening of the safety device.

According to a particularly preferred embodiment, the safety device comprises at least one spring element. The spring element is preferably operatively connected to the syringe member and counteracts the movement of the syringe member relative to the safety device. This means that, if a user of the syringe moves the syringe member relative to the safety device, the spring element counteracts this and, if the relative movement is suppressed, would move the syringe member relative to the safety device back into a position in which the entire syringe is back in the safety device.

The spring element can therefore ensure that the needle can be securely moved back into the safety device after the syringe has been used, and that the guided pin can be moved into the final position, preferably automatically.

In this case, the spring element can have various designs. The spring element is preferably a spiral spring.

According to a preferred embodiment, the safety device is at least operatively connected to the syringe member by means of a mounting element. In this case, it is conceivable for the guided pin(s) to be arranged on the mounting element. Here, it is advantageous for the mounting element to be connected on one side to a needle attachment, which is connected to the syringe member, and to be connected on the other side to the safety device by means of the at least one guided pin, since the guided pin is arranged inside the guide slot of the safety device.

The mounting element is particularly advantageously arranged inside a sleeve of the safety device. More advantageously, this sleeve also comprises the guide slot.

According to a preferred embodiment, the safety device, in particular the sleeve, comprises two recesses and the mounting element comprises two guided pins, the recesses and the guided pins advantageously being opposite one another, thus ensuring particularly advantageous guiding.

More preferably, the spring element is also arranged inside the sleeve and is particularly preferably secured inside the sleeve by means of the mounting element such that it cannot fall out.

The first slot region advantageously comprises a first curved guide slot portion and the second slot region advantageously comprises a second curved guide slot portion, on which portions the guided pin is guided, depending on its position in the guide slot. The particular guide slot portion can advantageously comprise a plurality of sub-portions.

Since the slot regions can comprise curved guide slot portions, it is advantageous for the mounting element to no longer be able to move axially but to be able to rotate radially around the syringe member when mounted on the syringe member. This ensures that the guided pin can follow the course of the particular guide slot. This therefore means that the mounting element and consequently also the guided pin can rotate around the syringe member during a relative movement.

According to a further preferred embodiment, a separating region is adjacent to the first and the second slot region. More advantageously, this separating region can be arranged between the first and the second slot region, at least in part.

The separating region is particularly preferably designed such that it comprises an apex, which lies on the notional separation line. This apex is advantageously a local extremum of the separating region, and therefore movement of the guided pin can be supported as a result. Since the apex lies on the dividing line, the first and the second slot region can be easily defined by the separating region and the dividing line. In addition, since the apex is preferably a local extremum, the guide of the guided pin is guided counter to the longitudinal direction of the syringe member in particular, since the apex defines in the region around the apex into which slot region the guided pin is guided.

According to a particularly preferred embodiment, when the guided pin is in the second slot region, it can be moved into a final region by means of a guide slot of the second slot region. The guided pin can preferably be operatively connected to a stop element in this final region.

The guide slot of the second slot region is advantageously the second guide slot portion.

This therefore means that, when the guided pin is in the second slot region, it is moved into the final region by means of the second slot region and preferably by means of the spring element, and is then operatively connected to the stop element.

The stop element is designed here such that, when the guided pin is in the final position, it can no longer move in the longitudinal direction towards the distal end of the needle, thus preventing the needle from being moved out the safety device any further.

According to a preferred embodiment, the stop element therefore comprises an apex, which lies on a line that is perpendicular to the dividing line. This means that the line extends in a width direction of the syringe member. The line can also be referred to as the transverse line. The stop element with the apex particularly advantageously also extends in the direction of this transverse line. This means that the stop element is essentially at a 90° angle to the separating region.

By arranging such a stop element, it is therefore not possible for a syringe that has already been used, i.e. a syringe whose pricking element has already left the safety device, to be used again for an injection procedure. Likewise, a patient or third-party user is no longer able to injure themselves on the pricking element, both before and after the injection procedure, since the pricking element is surrounded by the safety device in each case.

In addition to the safety device described thus far, according to a preferred embodiment, it is therefore also conceivable for the safety device to comprise a cap element and/or a needle guard. The cap element is advantageously provided with the needle guard. More advantageously, the cap element can be removed from the safety device before the syringe is used, the needle guard optionally also being removable together with said cap element. This can therefore make the safety device even safer for a person using the syringe, and can thus further reduce the risk of injury.

Additional advantageous embodiments can be found in the dependent claims.

Additional aims, advantages and expediencies of the present invention can be found in the following description in conjunction with the drawings, in which.

Figure 1:
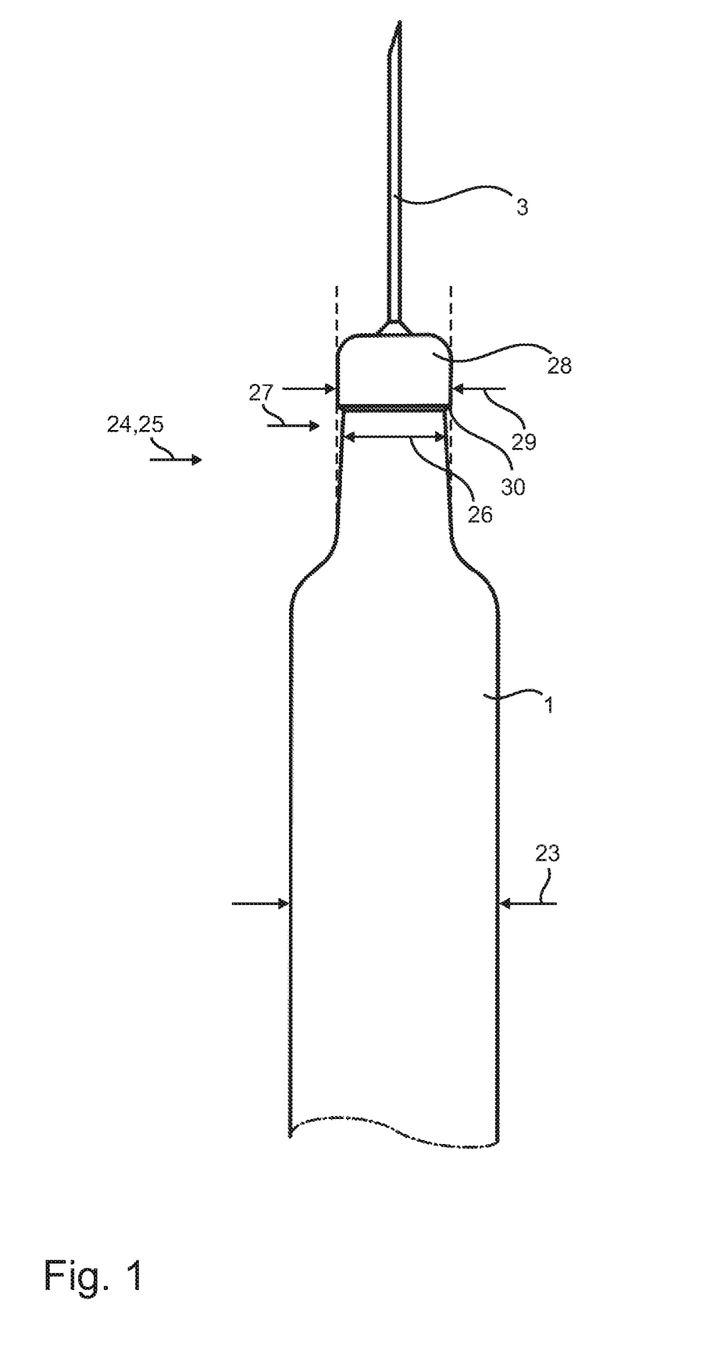
FIG. 1 is a section of the syringe member.

FIG. 1 shows a possible syringe member 1 that forms the basis of the invention. Commercially available syringe bodies 1 are substantially cylindrical, as is the syringe member 1 in the present case, and have a predetermined diameter 23. In this case, the syringe member 1 also comprises a narrowed region 25 at its distal end 24, which is also substantially cylindrical. In this case, however, the narrowed region 25 is in the shape of a truncated cone, the truncated-cone-shaped narrowed region having a diameter 26 at the cover surface (not shown here), i.e. the distal end 27 of the narrowed region 25, the diameter 26 of the narrowed region 25 being smaller than the diameter 23 of the syringe member 1.

Furthermore, in this case a needle holder 28 having a pricking element 3, a needle 3 in this case, is arranged at the distal end 27 of the narrowed region 25, said needle holder 28 having a diameter 29 that is greater than the diameter 26 of the narrowed region 25 but smaller than the diameter 23 of the syringe member 1. Furthermore, the needle holder 28 is arranged at the distal end 27 of the narrowed region 25 such that a transition region 30 is formed, the transition region 30 forming a region in which the diameter 26 of the narrowed region 25 and the diameter 29 of the needle holder meet and the diameter is thus intrinsically rapidly changed. The transition region 30 thus forms a type of projection.

Figure 2A:
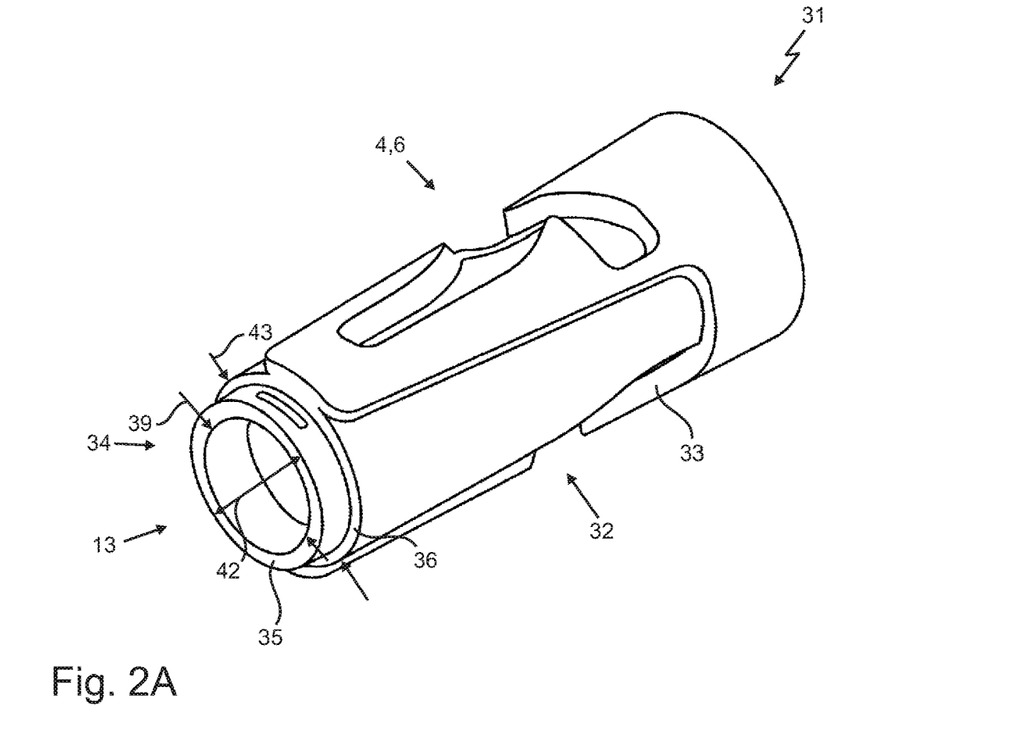
FIG. 2A is a perspective view of the sleeve.

FIG. 2A is a perspective view of a first important component of the safety device 2, specifically the sleeve 31. As can be seen clearly from FIG. 2A, the sleeve comprises a recess 4, which forms the guide slot 6 for guiding the guided pin 5 (not shown in this case). In addition, the sleeve can comprise a recessed region 32, which is delimited by an edge 33. An inversely recess 4' is advantageously arranged opposite the recess 4 in the sleeve 31 and an inversely recessed region 32' is advantageously arranged opposite the recessed region 32 on said sleeve.

In this case, the recessed region 32 allows a cap element 21 (see FIG. 2B) to be attached guided to increase the safety of the safety device 2. The cap element 21 is at least in operative contact with and preferably at least non-positively connected to the sleeve 31 by means of the edge 33 of the recessed region 32.

Figure 2B:
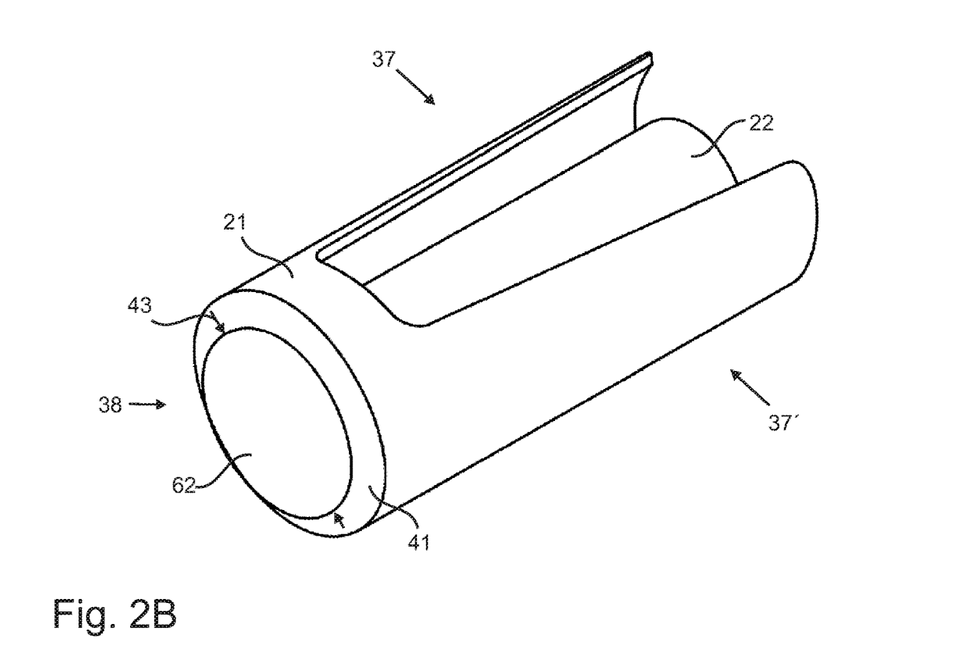
FIG. 2B is a perspective view of the cap element.

The sleeve 31 preferably comprises an exit opening 13 at the distal end 34 thereof, which is formed as an annulus 35 in this case, the sleeve 31 being continued by an annular region 36 thereof. In this case, the annular region 36 has a larger diameter than the annulus 35. The annulus 35 and the annular region 36 are particularly advantageously arranged concentrically with one another. The cap element 21 is advantageously designed such that it can be placed on the annulus 35 but not on the annular region 36, and therefore, when the cap element 21 is attached, the cap element 21 is in contact with both the annulus 35 and the annular region 36 and the attachment movement of the cap element 21 is limited by this design.

FIG. 2B shows the cap element 21 in its already truncated form, as before. In this case, the cap element 21 also comprises a needle guard 22 and a first wing element 37 and a second wing element 37', which are designed so as to be complementary to the recessed region 32 and to the inversely recessed region 32', respectively.

The needle guard 22 is preferably substantially cylindrical and is or can be advantageously rigidly connected to the cap element 21, the needle guard 22 preferably being designed such that the needle guard 22 can be inserted into the annulus 35. This therefore means that an external diameter 40 (not shown in this case) of the needle guard 22 corresponds to at most the internal diameter 39 of the annulus 35. However, it is conceivable for other geometric shapes to be used instead of a circle.

The distal end 38 of the cap element 21 is also designed as an annulus 41 in this case, the internal diameter 43 of which corresponds to no less than the external diameter 42 of the annulus 35 and no more than the external diameter 43 of the annular region 36. This means that the annulus 41 comes to lie on the annular region, thus operatively connecting it thereto.

Figure 3A:
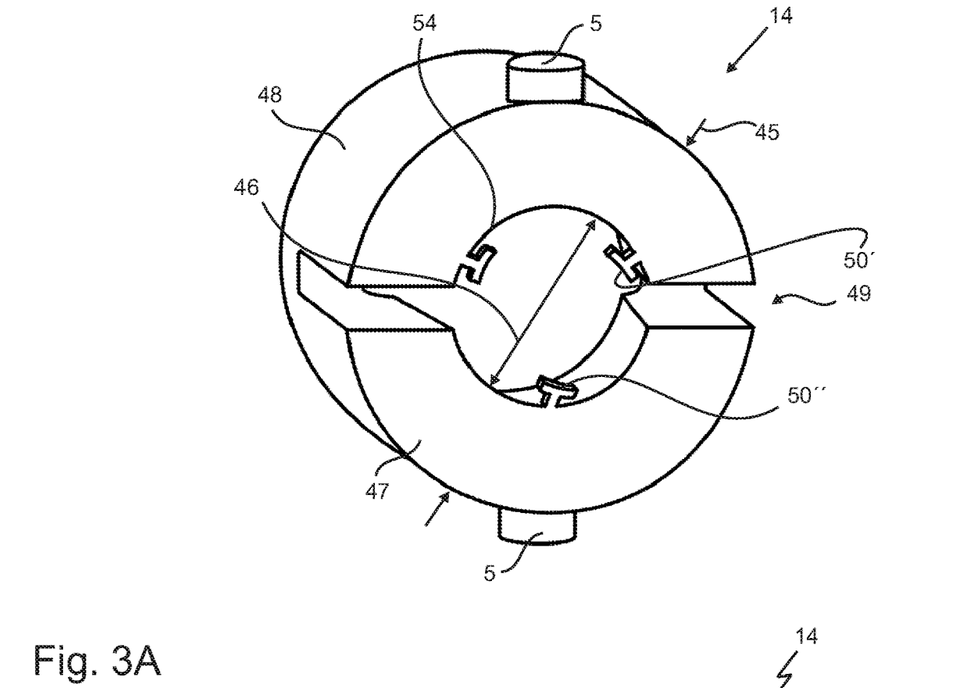
FIG. 3A is a perspective view of the mounting element from above.
Figure 3B:
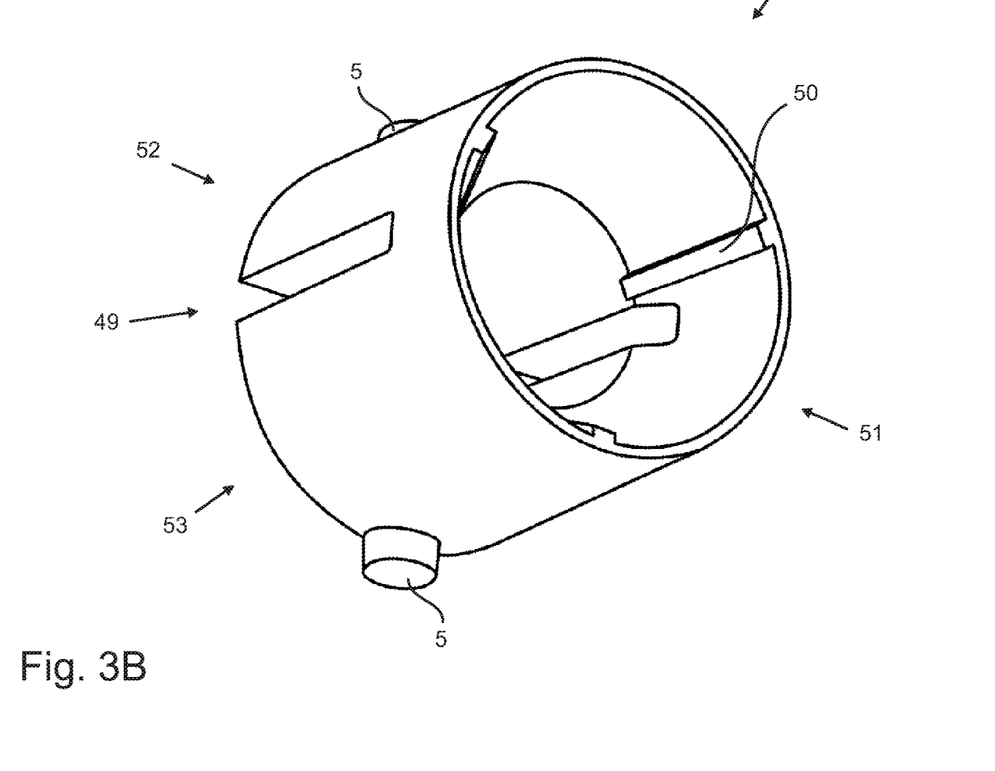
FIG. 3B is a perspective view of the mounting element from below.

FIGS. 3A and 3B show the mounting element 14, by means of which the sleeve 31 and therefore the safety device 2 can be connected to the syringe member 1 as a whole, FIG. 3A being a perspective view from above of the mounting element 14 and FIG. 3B being a perspective view from below of the mounting element 14.

The mounting element 14 is substantially cylindrical in this case, having an external diameter 45 and an internal diameter 46. Reference numeral 47 denotes the distal end of the mounting element 14.

In this case, two guided pins 5 are arranged on a lateral surface 48 of the mounting element 14, which lie on opposite sides of the mounting element 14. Said guided pins 5 can then be arranged in the gate 6 of the sleeve and be operatively connected thereto.

In addition, the mounting element 14 comprises one or more, in this case two, cut-outs 49 and one or more, in this case three, latching elements 50, the function of which is outlined below with reference to FIG. 3B.

In FIG. 3B, reference numeral 51 denotes a proximal end 51 of the mounting element 14. As can be seen, the latching elements 50 of the mounting element 14 extend so as to increase in size from the proximal end 51 towards the distal end 47, i.e. the latching elements are larger at the distal end 47 than at the proximal end 51 when viewed in the radial direction.

If, when joining the mounting element 14 and the syringe member 1, in particular the narrowed region 25 thereof, the mounting element 14 is first pushed onto the needle holder 28 by its proximal end 51, a first half 52 and a second half 53 of the mounting element 14, which are separated by the cut-outs 49, are moved away from one another as a result of the difference in thickness in the radial direction that increases in the axial direction. It is therefore necessary here for the mounting element 14 to be at least partially resilient.

If the distal end 47 of the mounting element 14 passes the transition region 30, the first 52 and the second 53 halves move towards one another as a result of the resilient design, so that the mounting element 14 and therefore the safety device 2 are ultimately clipped onto the syringe member 1.

In order to secure this clip connection, the latching elements 50 comprise securing portions 50" at their distal end 50', which portions extend in the circumferential direction of an inner circle 54 of the mounting element 14 and are mechanically operatively connected to the transition region 30.

The safety device 2 comprising the sleeve 31, the mounting element 14 and the cap element 21 can particularly preferably be pre-mounted and can be connected as a whole to the syringe member 1 by means of the mounting element 14.

Figure 4:
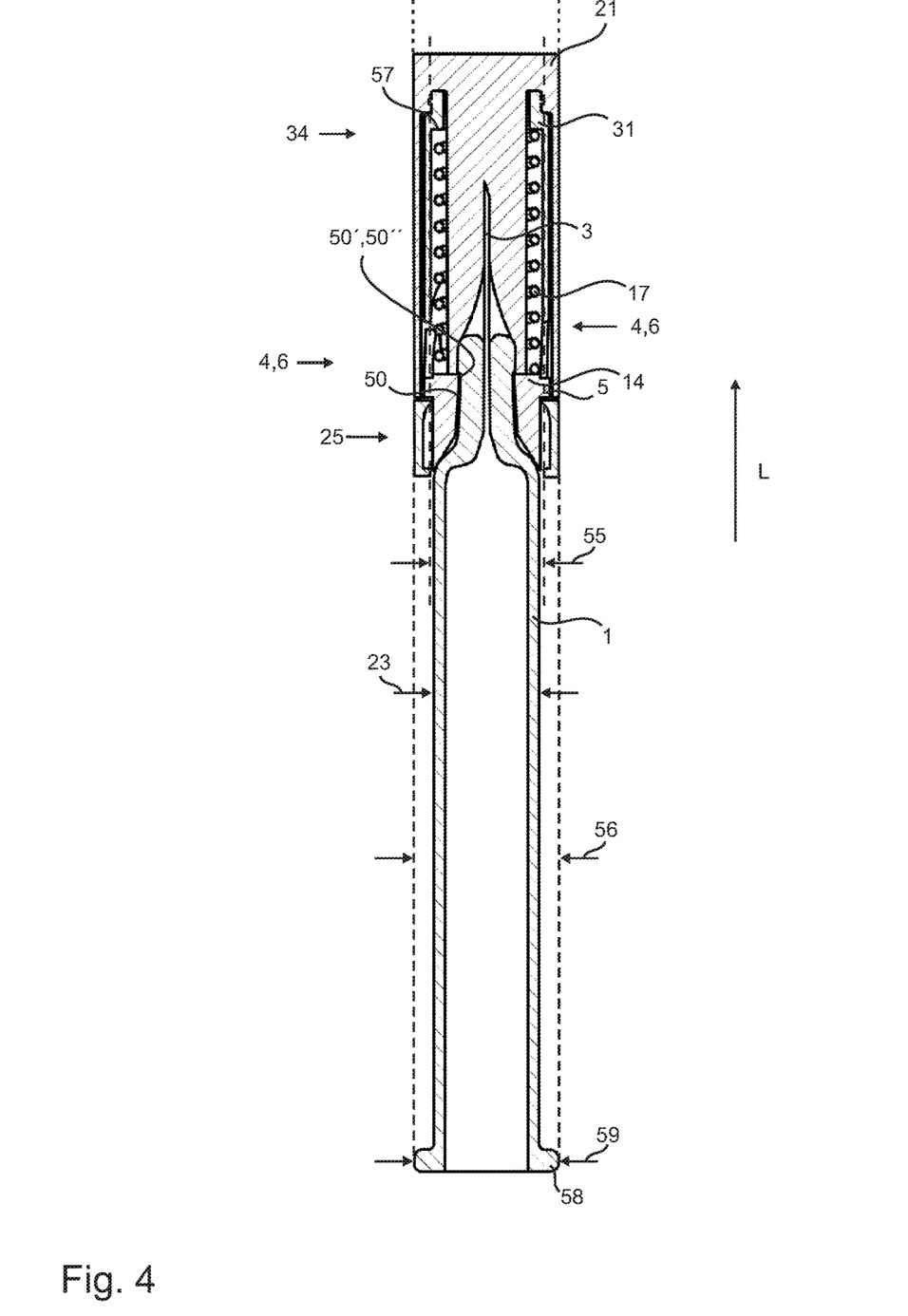
FIG. 4 is a longitudinal section of a syringe member comprising the safety device mounted thereon.

FIG. 4 is a longitudinal section of a syringe member 1 comprising a safety device 2 mounted thereon.

In addition to the cap element 21, the sleeve 31 and the mounting element 14, the safety device 2 comprises a spring element 17 here, which is formed as a spiral spring 17 in this case.

As can clearly be seen, the guided pins 5 are in contact with the recess 4 or the guide slot 6, so that the guided pins are guided by the guide slot when the syringe member moves relative to the safety device.

The mounting element 14 is clipped together with the narrowed region 25 by means of the latching elements 50 and the securing portions 50" thereof, and is connected to the sleeve 31 by means of the guided pins 5.

The sleeve 31 also comprises an internal bearing region 57 at its distal end 34, which can be operatively connected to the spring element 17. The spring element 17 is therefore held in the sleeve 31 by the bearing region 57 on one side and by the mounting element 14 on the other side, and is thus secured against falling out.

The safety device 2 is dimensioned such that the sleeve 31 has an internal diameter 55 that is greater than the diameter 23 of the syringe member 1, and therefore the syringe member 1 can be moved into the sleeve 31 when it moves forwards in the longitudinal direction L, the movement direction being shown by an arrow, relative to the safety device 2. At the same time, the external diameter 56 of the sleeve 31 or of the safety device 2 is selected so as to correspond to no greater than a maximum diameter of a retaining apparatus 58, which is attached to the proximal end of the syringe member 1 and is intended for retaining and securely positioning the syringe. The purpose of this size restriction is outlined in more detail with reference to FIG. 6.

With reference to FIG. 5A-5E, the safety device 2 is depicted in detail again, in particular the movement of the guided pin 5 and of the syringe member 1 relative to the safety device 2 and the position of the needle 3. For the sake of clarity, the safety device 2 is shown without the cap element 21 and the needle guard 22 in FIG. 5A-5E.

Figure 5A:
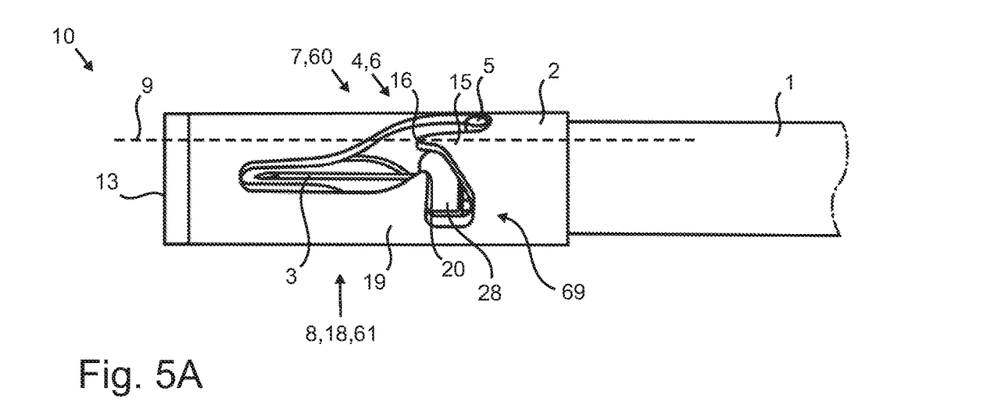
FIG. 5A shows a syringe in the starting position.

The arrangement consisting of the syringe member 1 and the safety device 2 in a starting position 10 can be seen in FIG. 5A. A starting position 10 is understood to mean a syringe that has not yet been used.

The guided pin 5 is also in a starting position 10 and is arranged in the first slot region 7. The first slot region 7 is separated from the second slot region 8 by the notional separation line 9 and from the separating region 15, which has an apex 16. The apex 16 lies on the notional separation line 9 in this case. The first slot region 7 comprises a guide slot portion 60 and the second slot region 8 comprises a second guide slot portion 61. The second slot region 8 also comprises a stop element 19.

In this case, the first slot region 7 is substantially L-shaped and comprises a curved first curve portion 60, the second slot region 8 being substantially L-shaped having a second curved curve portion 61, the second curve portion 61 being made up of several parts.

The distal end 34 of the sleeve is preferably placed directly on the skin so that the exit opening 13 is in contact with the skin. If the syringe member 1 is now moved in the longitudinal direction L relative to the safety device 2, the guided pin 5 is guided by the first guide slot portion 60, causing the mounting element 14 to be moved so as to surround the narrowed region 25. The mounting element 14 is therefore rigidly mounted in the axial direction, but can rotate freely in the radial direction around the narrowed region.

Figure 5B:
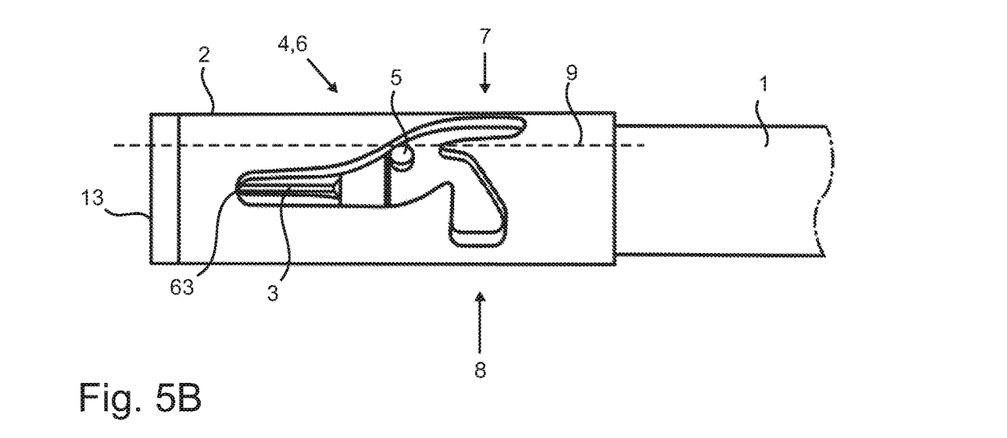
FIG. 5B shows the syringe according to FIG. 5A during movement of the guided pin.
Figure 5C:
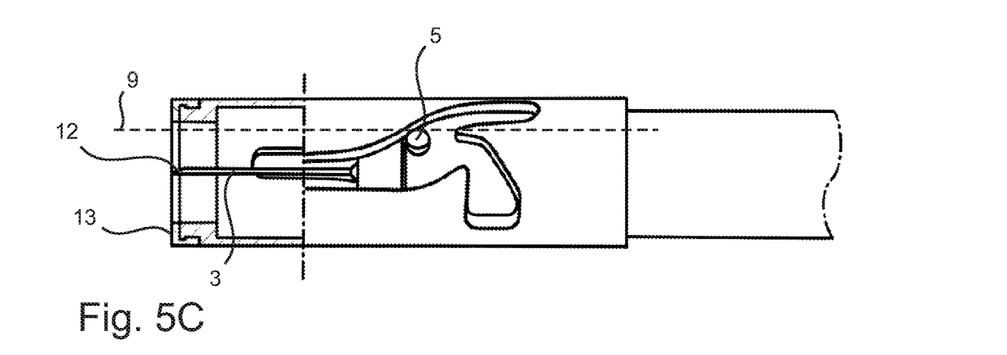
FIG. 5C is a longitudinal section of the syringe according to FIG. 5A during movement of the guided pin.

If the guided pin 5 passes the notional separation line 9, the guided pin 5 is moved from the first slot region 7 to the second slot region 8, as can clearly be seen in FIGS. 5B and 5C. During the movement of the guided pin, the distal end 12 of the pricking element 3 is arranged at the level of the exit opening 13. The pricking element 3 is therefore just about to leave the safety device 2, making an injection possible.

The pricking element 3 can then be moved further out of the safety device 2 until the guided pin 5 has reached a distal end 63 of the second slot region 8, thereby preventing further movement in the longitudinal direction.

Figure 5D:
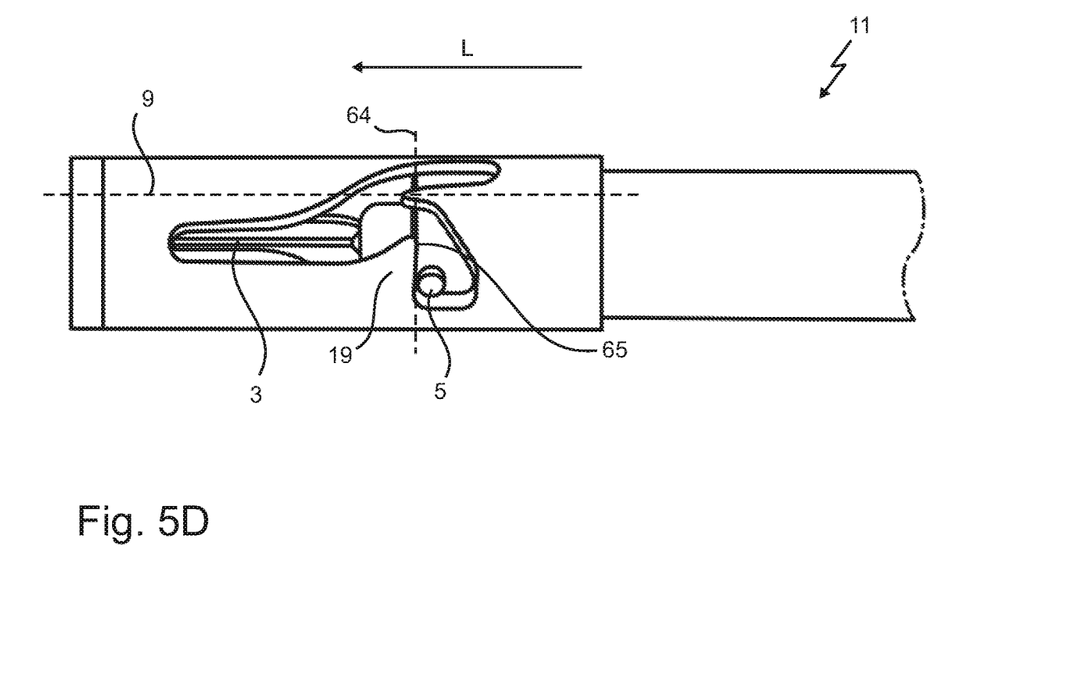
FIG. 5D shows the syringe according to FIG. 5A in the final position.
Figure 5E:
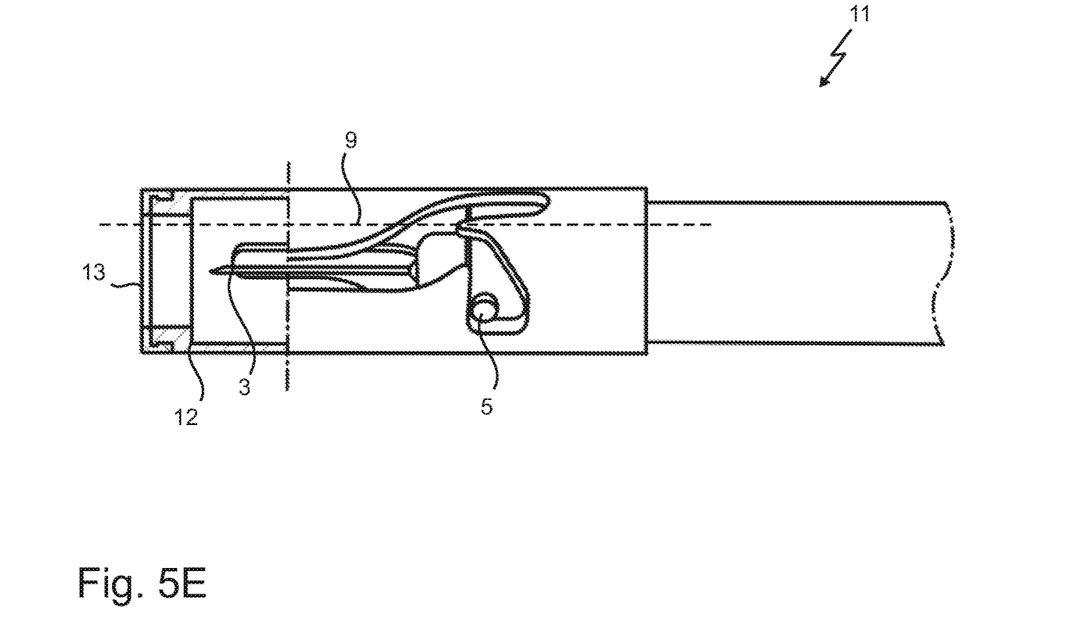
FIG. 5E is a longitudinal section of the syringe according to FIG. 5A in the final position.

If the injection has been carried out and the pricking element 3 has been moved out of the safety device 2, the user reduces the pressure on the syringe, as a result of which the syringe member 1 is moved counter to the longitudinal direction L relative to the safety device 2 by the spring force of the spring element 17. The pricking element is therefore automatically moved back into the safety device 2 by means of the spring element 17. In this case, depending on the extent to which the pricking element 3 has been moved out of said safety device, the guided pin 5 moves along the second guide slot portion 61 and/or on a line (not shown in this case) that extends in parallel with the longitudinal direction.

Once the guided pin 5 has passed a certain position in the second slot region 8, the guided pin 5 is in contact with the second guide slot portion 61 and is guided thereby. The second guide slot portion is designed so as to automatically move the guided pin into a final position 11 with the assistance of the return movement by the spring element 17, and is in contact with a stop element 19. The stop element 19 preferably comprises an apex 20, which is arranged on the transverse line 64 that extends perpendicularly to the separation line 9. The apex 20 is used to guide the guided pin 5 inside the second slot region 8 more effectively. In this case, the stop element also comprises a portion 65 which the guided pin 5 abuts. In this case, said portion 65 also lies on the transverse line 64, but other embodiments of the portion 65 are also conceivable. For example, the portion 65 can also have a curved path.

In this case, the portion 65 should always be shaped such that, in an attempt to re-operate the syringe, the guided pin 5 remains in its final position 11.

Figure 6:
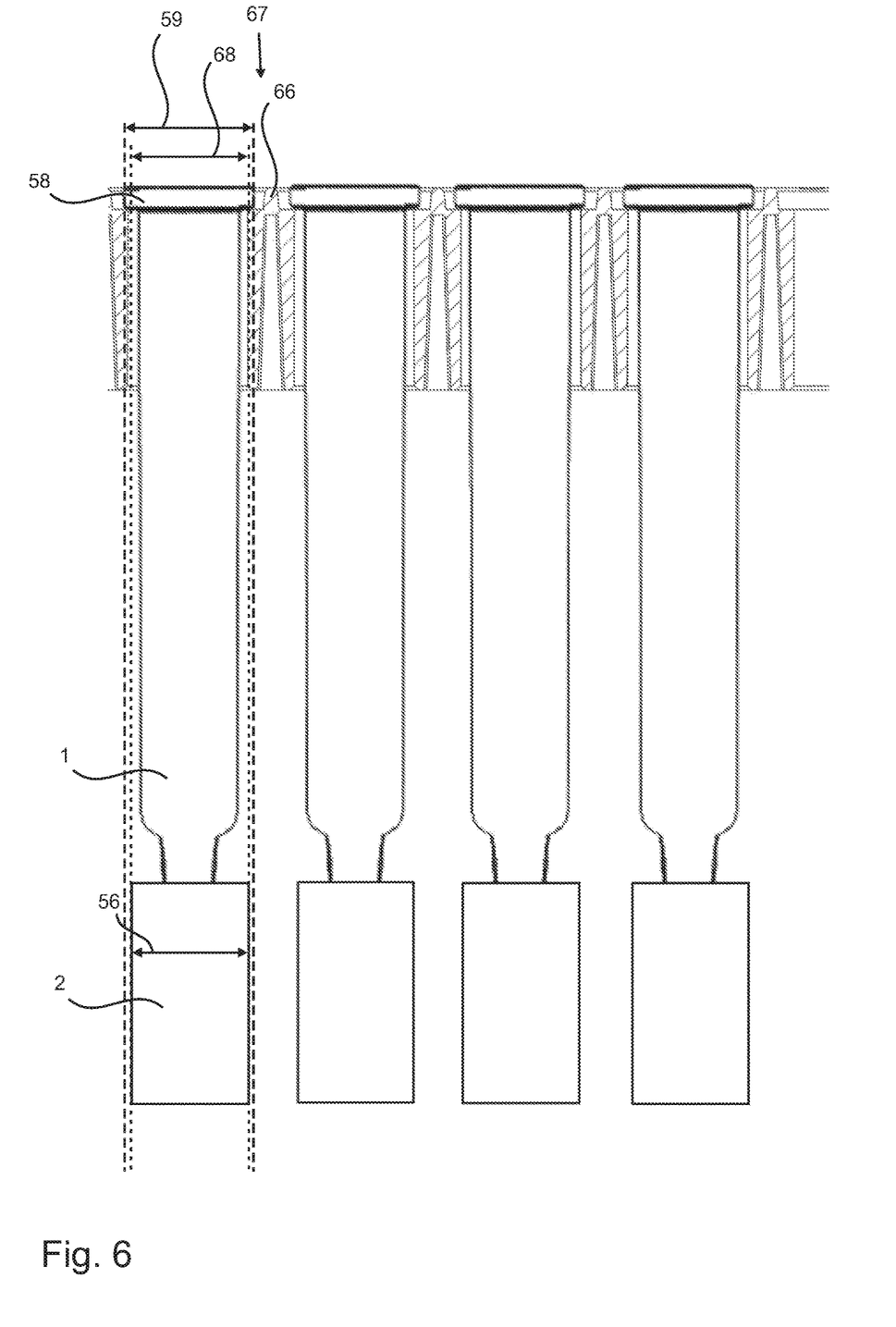
FIG. 6 shows a syringe mounted in a syringe nest and comprising a syringe member and a safety device.

For FIG. 6, reference is made to FIG. 4, where the advantageous dimensions of the safety device 2 have been described. A section of a syringe nest 66 can also be seen, the syringes each being mounted in an opening 67 of the syringe nest 66. In order to be able to mount a syringe in the syringe nest 66, the diameter 59 of the retaining apparatus is selected to be greater than the diameter 68 of an opening 67. In order to be able to mount the syringe member 1 together with the safety device 2 in an opening 67, the external diameter 56 of the sleeve 31 and the external diameter 56 of the safety device 2 therefore have to be selected to be smaller than the diameter 59 of the retaining apparatus 58. It is therefore possible to already mount the syringe in the syringe nest together with the safety device 2, and to fill and sterilise it therein.

All of the features disclosed in the application documents are claimed to be essential to the invention provided that they are novel over the prior art, either individual or in combination.

LIST OF REFERENCE NUMERALS 1 syringe member
2 safety device
3 piercing element
4 recess
4' inversely recess
5 guided pin
6 guide slot
7 first slot region
8 second slot region
9 notional separation line
10 starting position
11 final position
12 distal end of the pricking element
13 exit opening
14 mounting element
15 separating region
16 apex of the separating region
17 spring element
18 guide slot of the second slot region
19 stop element
20 apex of the stop element
21 cap element
22 needle guard
23 diameter of the syringe member
24 distal end of the syringe member
25 narrowed region of the syringe member
26 diameter of the narrowed region
27 distal end of the narrowed region
28 needle holder
29 diameter of the needle holder
30 transition region
31 sleeve
32 recessed region
32' inversely recessed region
33 edge
34 distal end of the sleeve
35 annulus
36 annular region
37 first wing element
37' second wing element
38 distal end of the cap element
39 internal diameter of the annulus 40 external diameter of the needle guard
41 annulus
42 external diameter of the annulus
43 internal diameter of the annulus
44 external diameter of the annular region
45 external diameter of the mounting element
46 internal diameter of the mounting element
47 distal end of the mounting element
48 lateral face of the mounting element
49 cut-out
50 latching element
50' distal end of the latching element
50" securing portion
51 proximal end of the mounting element
52 first half of the mounting element
53 second half of the mounting element
54 inner circle
55 internal diameter of the sleeve
56 external diameter of the sleeve
57 bearing region
58 retaining apparatus
59 diameter of the retaining apparatus
60 first guide slot portion
61 second guide slot portion
62 distal end of the cap element
63 distal end of the guide slot
64 transverse line
65 portion of the stop element
66 syringe nest
67 opening
68 diameter of the opening

The invention claimed is:

1. A syringe member comprising a safety device arranged at one end of said member for preventing pricking injuries, the syringe member comprising a pricking element that is arranged at one end thereof and has a distal end, and the safety device comprising a sleeve, at least one guided pin, and at least one recess, which forms a guide slot for guiding the at least one guided pin in a longitudinal direction of the syringe member when the syringe member moves relative to the safety device, wherein the sleeve comprises an exit opening at its distal end, wherein the at least one guided pin being arranged in a first slot region of the guide slot in a starting position, in which the distal end of the pricking element is arranged inside the safety device, and the at least one guided pin being arranged in a second slot region of the guide slot in a final position, in which the distal end of the pricking element is moved out of the safety device through the exit opening of the sleeve,
wherein
a separating region having an apex is arranged, at least in part, between the first and the second slot region, and a notional separation line that separates the first and the second slot region extending in the longitudinal direction through the apex,
the first slot region comprising a first curved portion, on which the at least one guided pin is guided as far as the notional separation line as a result of the relative movement of the syringe member,
the second slot region comprising a second curved portion, on which the at least one guided pin is guided, as a result of the relative movement of the syringe member, once said at least one guided pin has passed the notional separation line, wherein the distal end of the pricking element being arranged at the level of the exit opening of the safety device as said pin passes the notional separation line,
wherein once the distal end of the pricking element has passed the level of the exit opening, the at least one guided pin is in the second slot region, in which the at least one guided pin may only be moved to a distal end region of the second slot region or to a final region of the second slot region, wherein the at least one guided pin is moved automatically into the final region by at least one spring element, which is operatively connected to the syringe member and counteracts the movement of the syringe member relative to the safety device, wherein in the final region the at least one guided pin is operatively connected to a stop element, wherein the stop element comprises an apex, which protrudes into the second slot region.

2. The syringe member according to claim 1, wherein the at least one guided pin is arranged on a mounting element of the safety device.

3. The syringe member according to claim 2, wherein the syringe member and the safety device are interconnected by means of the mounting element.

4. The syringe member according to claim 1, wherein the stop element comprises an apex that lies on a line that is perpendicular to the notional separation line.

5. The syringe member according to claim 1, wherein the safety device comprises a cap element and a needle guard.

6. The syringe member according to claim 2, wherein the mounting element and the guided pin can rotate around the syringe member during a relative movement of the syringe member to the sleeve.

7. The syringe member according to claim 2, wherein the mounting element comprises one or more cut-outs and one or more latching elements, wherein the latching elements extend radially inwards, wherein the latching elements having a height in the radial direction, which increases from the proximal end towards the distal end, wherein the latching elements are in contact with the syringe member.

8. The syringe member according to claim 1, wherein the stop element comprises a portion, which the guided pin abuts, wherein said portion lies on a transverse line perpendicular to the notional separation line.

9. The syringe member according to claim 1, wherein second slot region is L-shaped.

10. The syringe member according to claim 5, wherein the sleeve comprises at least one recessed region, which is delimited by an edge, wherein the recessed region allows the cap element to be attached, wherein the cap element is at least in operative contact with the sleeve by means of the edge of the recessed region, wherein the cap comprises at least one wing like element, which is designed so as to be complementary to said recessed region and is arranged in said recessed region before the usage of the syringe member.

11. The syringe member according to claim 5, wherein the exit opening at its distal end is formed as an annulus, wherein from said annulus the sleeve being continued by an annular region, wherein the annular region has a larger diameter than the annulus, wherein the annulus and the annular region are arranged concentrically with one another, wherein the cap element is designed such that it can be placed on the annulus but not on the annular region, and therefore, when the cap element is attached, the cap element is in contact with both the annulus and the annular region and the attachment movement of the cap element is limited by this design.

12. The syringe member according to claim 11 wherein, the distal end of the cap element is designed as an annulus, wherein the internal diameter of the annulus corresponds to no less than the external diameter of the annulus of the exit opening and no more than the external diameter of the annular region of the sleeve, wherein the annulus of the cap element comes to lie on the annular region of the sleeve and operatively connecting it thereto.

13. The syringe member according to claim 11 wherein, the needle guard is cylindrically shaped and is rigidly connected to the cap element, wherein the needle guard is designed such that it can be inserted into the annulus of the sleeve, wherein an external diameter of the needle guard corresponds to at most an internal diameter of the annulus of the sleeve.

14. The syringe member according to claim 5 wherein in a state, where the cap element is attached to the sleeve, the needle guard encloses the pricking element, wherein the needle guard encompasses partially the distal end of the syringe member and contacts the mounting element.

* * * * *